United States Patent [19]

Loseff

[11] 4,246,899

[45] Jan. 27, 1981

[54] DRAINAGE SYSTEM FOR A COLLECTION OF BODY FLUIDS

[76] Inventor: Herbert S. Loseff, 308 Woodley Rd., Winnetka, Ill. 60093

[21] Appl. No.: 953,946

[22] Filed: Oct. 23, 1978

[51] Int. Cl.³ ............................................... A61M 1/00
[52] U.S. Cl. ..................................... 128/276; 128/764; 128/349 R; 128/350 R; 128/350 V
[58] Field of Search .................... 128/276, 349, 349 R, 128/349 B, 350 R, 350 V, 763, 764, 768, 771, 214 G

[56] References Cited

U.S. PATENT DOCUMENTS

| | | | |
|---|---|---|---|
| 2,607,347 | 8/1952 | Kleiner | 128/276 |
| 2,656,835 | 10/1953 | Eisenstein | 128/214 G |
| 2,896,629 | 7/1959 | Warr | 128/349 |
| 3,138,161 | 6/1964 | Allen | 128/349 B |
| 3,144,868 | 8/1964 | Jascalevich | 128/276 |
| 3,385,301 | 5/1968 | Harautuneian | 128/349 BV |
| 3,908,664 | 9/1975 | Loseff | 128/350 R |
| 4,155,350 | 5/1979 | Percavpio | 128/764 |
| 4,197,848 | 4/1980 | Garrett et al. | 128/349 R |

FOREIGN PATENT DOCUMENTS 2551010  5/1977  Fed. Rep. of Germany ...... 128/349 R

OTHER PUBLICATIONS

Catalog—Orthopedic Equipment Co., Bourbon, Indiana, 12/30/63.
Webster's Seventh New Collegiate Dictionary, G & C Merriam Co., Springfield, Mass., "integral", p. 439, 1963.

Primary Examiner—Robert W. Michell
Assistant Examiner—J. L. Kruter
Attorney, Agent, or Firm—Allegretti, Newitt, Witcoff & McAndrews

[57] ABSTRACT

A drainage system for a collection of body fluids is disclosed. The drainage system includes an elongated tubular member and an adapter member. The tubular member defines a drainage lumen, and drainage ports along its distal portion. The adapter member is sealed to the proximal portion of the tubular member. A drainage passageway within the adapter member communicates with the drainage lumen. A plug is sealed to an enlargement along the passageway. The plug is piercable by a needle-like drainage member to communicate a disposable evacuated container with the drainage lumen.

3 Claims, 11 Drawing Figures

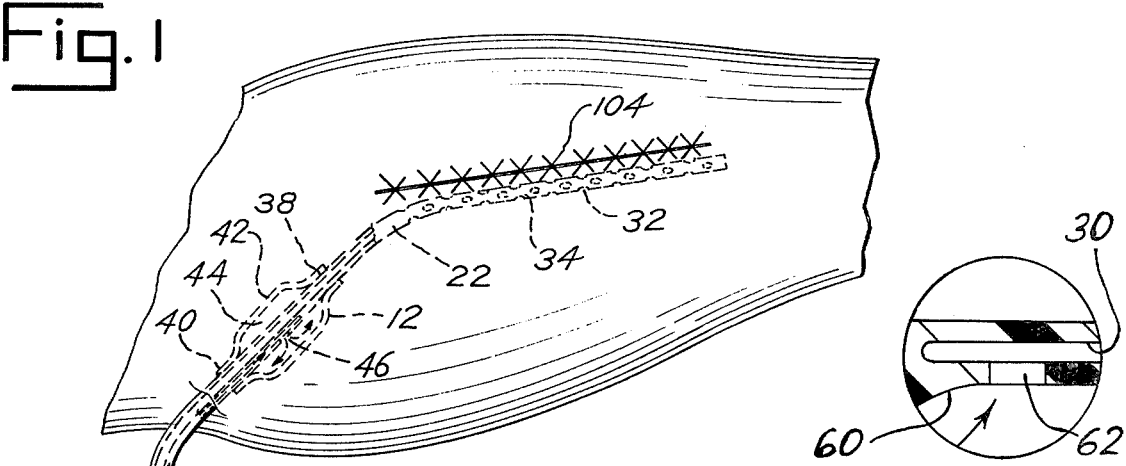
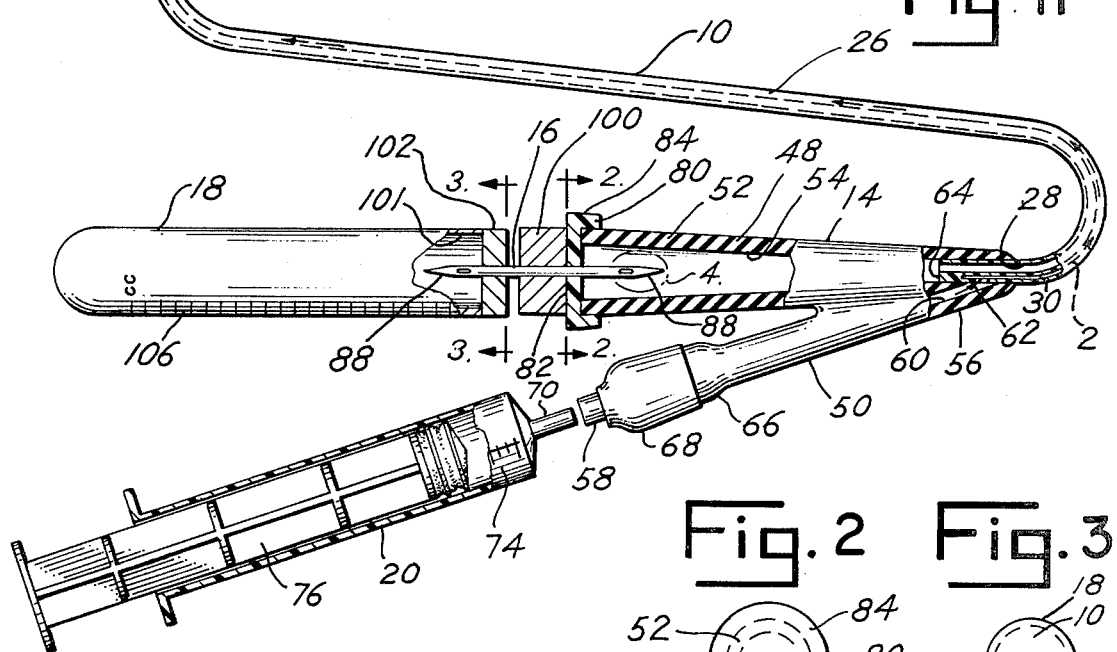
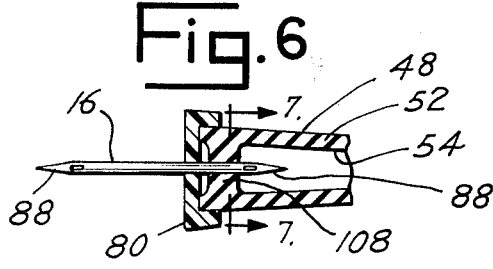
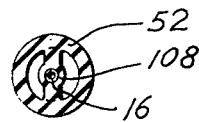
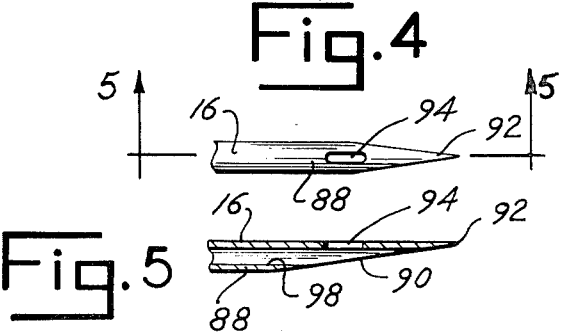

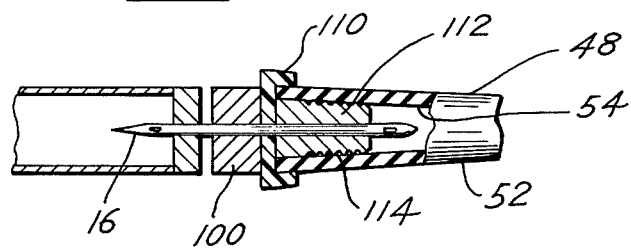
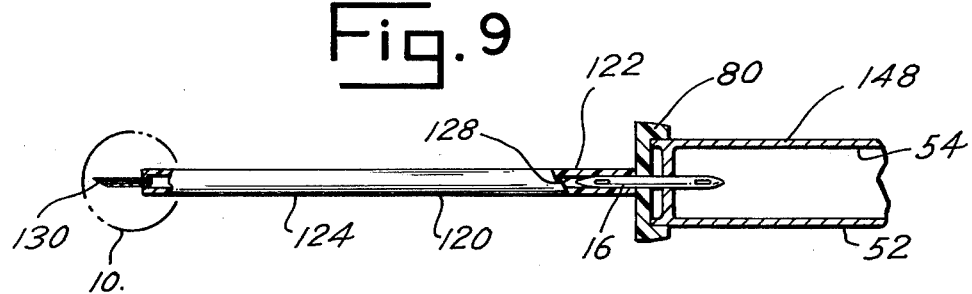
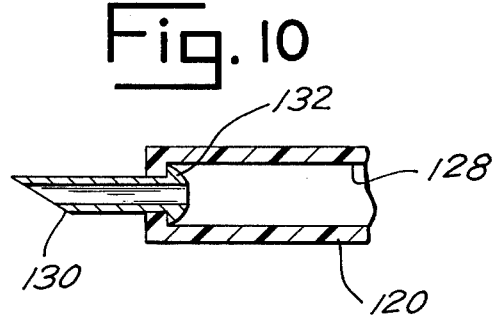

DRAINAGE SYSTEM FOR A COLLECTION OF BODY FLUIDS

BACKGROUND OF THE INVENTION

The present invention relates to body cavity drainage devices and the like, and more particularly, to a drainage system for a collection of body fluids including, as preferred, disposable, evacuated containers.

When a patient has a deep wound, or a large abscess, osteomyelitis or another collection of body fluids such as serum, blood or pus in the body, drainage catheter tubing (commonly known as wound tubing) is utilized to remove the collection. The wound tubing can be made of flexible plastic, such as polyethylene, or inert elastomers, such as silicone rubber or the like. The wound tubing is fabricated to have sufficient stiffness so that the collection can be removed through it by suction without collapsing the tubing. Suction is provided, as, for example, by an evacuator shown in U.S. Pat. No. 3,115,138.

The wound tubing typically has a large number of drainage ports or perforations for communication between a drainage lumen or bore of the tubing and its exterior, with the drainage ports being defined in a distal portion of the tubing. The wound tubing is passed through healthy, intact tissue adjacent the collection site in such a manner that the proximal portion of the wound tubing is positioned exterior of the patient, while the distal portion lies at the collection site. A desirable method of emplacing wound tubing is disclosed in U.S. Pat. Nos. 3,908,664 and 3,993,080.

Various significant problems are involved with prior art wound tubings, their associated evacuators and vacuum containers and the methods of their use. First, with reusable vacuum containers, it has become a practice to empty the containers at bedside. As a result, the possibility of contamination of the wound tubing is great.

Once initially filled, the containers are contaminated so that a treating physician cannot later obtain accurate wound drain cultures. Also, the maximum vacuum obtainable with typical reusable vacuum containers is about 30 mm Hg. This is insufficient to provice drainage for most applications and tends to promote clogging of the wound tubing, thereby requiring premature withdrawal of the wound tubing fom the wound site.

Further, because of a distaste for emptying the reusable vacuum containers, hospital personnel tend to service the containers infrequently. This also tends to promote clogging of the wound tubing, because the vacuum container frequently operates well below a maximum vacuum.

As a result of the problems associated with reusable vacuum containers, many physcians have chosen to utilize mechanical pumps connected to the wound tubing. These pumps do not overcome the disadvantage of requiring periodic emptying of containers, and, in addition, limit ambulation of patients because of their bulkiness. The maximum vacuum known with such pumps is about 50 mm Hg to 120 mm Hg. Experiments have been disclosed with about 750 mm Hg as a vacuum, but collapse of the wound tubing was reported.

SUMMARY OF THE INVENTION

In light of the significant problems associated with prior art devices, it is a principal object of the present invention to provide an improved drainage system for a collection of fluids within the body.

It is another principal object of the present invention to provide an improved body fluid drainage system which includes disposable vacuum containers.

Another object of the present invention is to provide an improved body fluid drainage system having vacuum containers which are disposable and sealed to prevent spillage.

Another object of the present invention is to provide an improved body fluid drainage system which is adapted to include disposable vacuum containers of varying sizes and vacuum magnitudes.

Another object of the present invention is to provide an improved body fluid drainage system which includes a needle permanently or semi-permanently in fluid communication with the drainage lumen of the wound tubing.

Another object of the present invention is to provide an improved body fluid drainage system which is readily adapted for use with a vacuum source other than disposable vacuum containers.

Another object of the present invention is to provide an improved body fluid drainage system which promotes the ambulation of the patient.

Still another object of the present invention is to provide an improved body fluid drainage system which is readily adapted for retro-flushing the wound tubing and the wound with a solution such as normal saline solution.

These and many other objects and advantages are satisfied by the present invention, which, in a principal aspect, is a drainage system for a collection of fluid within the body of a patient comprising, in brief, an elongated tubular member and an adapter member. The tubular member is elongated, with a distal portion and a proximal portion. The tubular member defines a drainage lumen, and drainage means along the distal portion for fluid communication between the drainage lumen and the exterior of the distal portion.

The adapter member is sealed to the proximal portion of the tubular member. The adapter member defines a drainage passageway in fluid communication the drainage lumen, and has an enlargement along the drainage passageway. A plug is sealed in the enlargement. The plug is piercable by a needle-like drainage member to place the drainage member in fluid communication with the drainage passageway.

The present invention may also include the needle-like drainage member pierced through the plug of the adapter member and in fluid communication with the drainage passageway. The drainage member has an exposed portion adapted to pierce a stopper member in an evacuated container.

The present invention may further include, in combination with the above, at least one disposable, evacuated container having a stopper member sealed thereto, which is pierced by the needle-like drainage member. This places the interior of the container in fluid communication with the drainage member, and thereby the drainage passageway, the drainage lumen, the drainage means and the exterior of the distal portion. With this arrangement and the distal portion positioned within the body, the collection of fluid is drained into the interior of the container, which may be disposed and replaced.

Preferably, the tubular member also defines an inflation lumen. The inflation lumen is in fluid communication with an elastomeric retention member. The retention member is carried on the tubular member adjacent the distal portion. When inflated, after the distal portion has been emplaced in the body, the retention member firmly retains the tubular member in situ. The adapter member defines an inflation passageway in fluid communication with the inflation lumen, and an instrument such as a syringe is attached to the adapter member, in fluid communication with the inflation lumen, to inflate the retention member.

In addition, the present invention may also include a second tubular member which is elongated, with a distal portion and a proximal portion. This second tubular member defines a second drainage lumen. The distal portion and the proximal portion may both be sealed, or one or both may have a needle-like drainage member in fluid communication with the second drainage lumen. The distal portion of the second tubular member is placed in fluid communication with the adapter member, and the evacuated container is placed in fluid communication with the proximal portion of the second tubular member. The evacuated container may thus be placed at a removed location.

With a wound drainage system as thus described, greatly increased sterility and convenience is achieved. The system is adapted for and includes disposable, evacuated containers, which substantially eliminate any distaste for servicing the system. Containers may be chosen in a size and vacuum appropriate for the collection of fluid being treated, and may be interchanged with containers of other sizes and vacuums as the condition of the collection progresses. The needle-like adapter member and plug remain in place, which increases the economy of the system. Uncontaminated cultures may be taken conveniently from the sealed, pre-sterilized containers. Ambulation of the patient is promoted. Also, the tubing and the collection site can be bathed or back-flushed with any desired solution, by rapid replacement of the evacuated container with a container of pressurized solution.

The objects and advantages of the present invention are more thoroughly understood from a detailed description of the preferred embodiments of the drainage system which follows.

BRIEF DESCRIPTION OF THE DRAWING

The preferred embodiments of the drainage system of the present invention will be described in relation to the accompanying drawing, wherein:

FIG. 1 is an illustrative view, with some portions broken away, showing a first preferred embodiment of the drainage system of the present invention as utilized;

FIG. 2 is a cross-sectioned view of the first preferred embodiment taken along line 2—2 of FIG. 1;

FIG. 3 is a cross-sectioned view taken along line 3—3 of FIG. 1;

FIG. 4 is a detail view of the area encircled by line 4 of FIG. 1;

FIG. 5 is a cross-sectioned view of the detail of FIG. 4, taken along line 5—5 in FIG. 4;

FIG. 6 is a fragmentary view of a second preferred embodiment of the drainage system of the present invention;

FIG. 7 is a cross-sectioned view taken along line 7—7 of FIG. 6;

FIG. 8 is a fragmentary view of a third preferred embodiment of the drainage system of the present invention;

FIG. 9 is a plan view of a fourth preferred embodiment of the drainage system of the present invention; and FIG. 10 is a cross-sectioned, detail view of the area encircled within line 10 of FIG. 9.

FIG. 11 is an enlarged view of the area encircled by line 11 of FIG. 1.

The terms "right," "left" and the like may be employed in the description which follows. Such directional and illustrative terms are intended as an aid to an understanding of the accompanying drawing, and shall not be limiting of the scope of the invention.

DETAILED DESCRIPTION OF THE PREFERRED EMBODIMENTS

Referring to FIGS. 1–10, four preferred embodiments of the drainage system of the present invention are depicted in the accompanying drawing, with the first depicted in FIGS. 1–5, the second in FIGS. 6–7, the third in FIG. 8 and the fourth in FIGS. 9–10. It should be understood that except insofar as otherwise described, the second, third and fourth preferred embodiments include all the details and features of the first preferred embodiment.

Referring now specifically to FIG. 1, the first preferred embodiment of the drainage system of the present invention includes a tubular member such as wound tubing 10, a retention member such as retention balloon 12, a needle-like adapter member such as needle adapter 14, a needle-like drainage member such as needle 16, an evacuated container such as tube 18, and a syringe-like instrument such as syringe 20. The needle adapter 14 is sealed to the wound tubing 10, as is the retention balloon 12. The needle 16 and syringe 20 are removably attached to the needle adapter 14, and the tube 18 is removably attached to the needle 16.

The wound tubing 10 is elongated, with a distal portion 22, a proximal portion 24, and an intermediate portion 26 between the distal portion 22 and the proximal portion 24. The wound tubing 10 defines a drainage lumen or bore 28, which is centrally located, substantially throughout its entire length. The wound tubing 10 also defines an inflation lumen 30 throughout the proximal portion 24 and the intermediate portion 26. The inflation lumen 30 is small in comparison with the drainage lumen 28, and extends alongside the drainage lumen 28. The inflation lumen 30 and the drainage lumen 28 do not communicate. I.e., the inflation lumen 30 and the drainage lumen 78 are separated from each other within the tubing 10.

The wound tubing 10 further defines a plurality of drainage openings or ports 32 along the distal portion 22. That is, a plurality of drainage ports 32 open through the wall 34 of the distal portion 22. The drainage ports 32 thereby communicate the exterior of the distal portion 22 with the drainage lumen 28. Preferably, the drainage ports 32 are of smaller aperture size than the drainage lumen 28, so as to screen potentially obstructing masses from the drainage lumen 28.

The elastomeric retention balloon 12 is carried on the intermediate portion 26, adjacent the distal portion 22. As preferred, the retention balloon 12 consists of an annular sleeve sealed to the exterior of the wound tubing 10 at either end 38, 40. The mid-section 42 of the retention balloon 12 defines an underlying free space 44 about the exterior of the tubing 10 between the ends 38, 40. A distal inflation opening 46 communicates the terminus of the inflation lumen 30 with the free space 44 through the wall 34 of the wound tubing 10.

Both the wound tubing 10 and the retention balloon 12 are most preferably silicone rubber. Such material is sufficiently stiff to avoid collapse of the wound tubing 10 when suction is applied to the drainage lumen 28, is flexible and resilient, and is non-adherent and non-reactive.

The needle adapter 14 includes a main drainage body 48 and an integral inflation arm 50. As used herein, the term "integral" means formed as a unit or unified structure. The drainage body 48 and arm 50 are thus formed as a unit. The drainage body 48 has a tapered or frusto-conical wall 52. The drainage body 48 is hollow, with a wall 52 defining a drainage passageway 54. The inflation arm 50 angles or branches off the drainage body 48 from the smaller diameter portion of the drainage body 48. The inflation arm 50 is also hollow, with a substantially cylindrical wall 56 defining an inflation passageway 60.

The needle adapter 14 is sealingly secured at a distal end to the end of the proximal portion 24 of the wound tubing 10. The drainage lumen 28 is in open communication with the drainage passageway 54. A proximal inflation opening 62, shown best in FIG. 11, communicates the inflation lumen 30 with the inflation passageway 60. A seal 64 separates the inflation lumen 30 from the drainage passageway 54.

The inflation arm 50 has a free end 66, within which a one-way check valve (not shown) is located, inside a valve body 68. The check valve permits fluid flow in the inflation arm in a direction toward the inflation lumen 30, and substantially prevents fluid flow in the opposite direction. As conventional, the valve is provided for deflation of the balloon 12.

A hollow, cylindrical syringe fitting 58 is attached to the valve body 68, for receiving the tip 70 of the syringe 20. As typical, the syringe 20 has a syringe body 74 and a plunger 76 slidably mounted within the syringe body 74. Advancement of the plunger 76 within the body 74 forces fluid ahead of the plunger 76 out the tip 70.

A plug such as cap 80 is sealed to the enlarged, proximal end of the drainage body 48. The cap 80 includes a central, disc shaped portion 82 across the open end of the drainage passageway 54 and an integrally formed, flange portion 84 about the end of the wall 52. The cap 80 is material readily piercable by a needle or needle-like member, such as rubber or the like.

The drainage needle 16 is inserted through the cap 80. As shown in FIGS. 1, 4 and 5, the needle 16 is hollow end-to-end. Each end 88 is sharply pointed. An edge 90 is cut across the end 88, at slight angle to the longitudinal axis of the needle 16, so as to define an extreme tip 92 along one side of the needle 16. Adjacent the tip 92 and opposite the edge 90 is an aperture 94. The central channel 98 of the needle 16 is open to the drainage passageway 54 through the aperture 94 and the edge 90. A grip 100, of hard rubber or the like, surrounds the mid-section of the needle 16 to provide facile gripping and manipulation of the needle 16.

The needle 16 is also inserted through the stopper 102 of the tube 18. The tube 18 is glass, plastic or the like, and the stopper 102 is sealed into the open end of the tube 18. Prior to sealing, the interior 101 of the tube 18 is evacuated. When the needle 16 is inserted into the interior 101, the central channel 98 communicates through the aperture 94 and the edge 90 with the interior 101. A vacuum is thus exerted in the central channel 98, which results in a vacuum being exerted in the drainage passageway 54, the drainage lumen 28 and thereby the drainage ports 32. Fluid collected adjacent the distal portion 22 of the wound tubing 10, as in the wound site 104, flows through the system into the tube 18. When the tube 18 is filled, as may be visually observed and measured against the volume calibrations 106, the tube 18 is removed and replaced. The needle 16 remains firmly in place within the cap 80, ready to pierce the stopper of a new tube.

The replacement of the tube 18 is speedily accomplished, and thus exposure to fluid from the wound site 104 is at a minimum. The tube 18 may be disposed or utilized for an uncontaminated culture, because the stopper 102 substantially closes the opening from which the needle 16 is withdrawn. If a number of tubes such as tube 18, of different sizes, are sterilized and evacuated, to different vacuum strengths, a selection can be made of a tube having a size and vacuum appropriate for the collection of fluid under treatment. The tubing 10 may be back flushed by replacing the tube 18 with a tube filled with solution under pressure. If desired, the proximal portion of the drainage body 48 can be cut away, to provide suction by a conventional means, such as a Gomco, Emerson or wall suction.

Referring now to FIGS. 6-7, the second preferred embodiment of the drainage system of the present invention includes a needle support 108 integrally formed within the proximal portion of the main drainage body 48. As shown in FIG. 7, the support 108 bridges the drainage passageway 54 from opposite sides of the wall 52. The needle 16 is inserted through the support 108 and permanently, or semipermanently, retained therein.

In contrast with the first preferred embodiment, the needle 16 in the second preferred embodiment is permanently assembled with the needle adapter 14. The grip 100 is thus eliminated. Sterility of the needle 16 is maintained by a removable cover (not shown) temporarily placed over the exposed end of the needle 16. Insertion of the needle 16 into a tube 18 is facilitated by gripping the proximal end of the needle adapter 14.

As shown in FIG. 8, the third preferred embodiment includes a needle assembly 110 which comprises the needle 16, the grip 100, the cap 80 and an insertion piece 112. The proximal end of the main drainage body 48 has the drainage passageway 54 exposed. The insertion piece 112 is tapered, and has circumferential ridges 114 along its outer surface. In use, the assembly 110 is joined to the body 48. The ridges 114 press against and expand the wall 52 of the body 48 to firmly retain the union of the assembly 110 and the body 48.

Referring finally to FIGS. 9-10, the fourth preferred embodiment includes extension tubing 120, which, like tubing 10, has a distal end 122, a proximal end 124 and a drainage lumen or bore 128. At its distal end 122, the tubing 120 is sealed, and at its proximal end 124, the tubing 120 includes a needle 130. The needle 130 is in communication with the lumen 128, and has an exposed end adapted to pierce a stopper 102. A flange 132 is formed on the needle 130, to abut the extreme end of the tubing 120, thereby keeping the needle 120 joined to the tubing 120. In use, the sealed, distal end 122 of the tubing 120 is pierced by the needle 16 to communicate the drainage passageway 54 with the drainage lumen 128. The needle 130 is pierced through a stopper 102, and the interior of a tube 18 is thus in communication with the drainage ports 32. The extension tubing 120 is thus adapted to provide for remote placement of the tube 18.

As described, the extension tubing 120 is highly useful with a needle 16 and needle adapter 14 as in the second preferred embodiment. By sealing either or both ends 122, 124, and by joining a needle 130 to either or both ends 122, 124, the tubing 120 is readily adapted to other needle and needle adapter assemblies.

As most preferred, the method of the present invention is practiced with one of the four preferred embodiments of the drainage system as described. For example, with the first preferred embodiment, a number of tubes 18 are evacuated to a vacuum within a principal range of 150 mm Hg to 650 mm Hg, and most preferably to a vacuum within a range of 165 mm Hg to 650 mm Hg. The distal portion 22 of the wound tubing 10 is emplaced within the wound site 104, for drainage of body fluids which collect there, if any. A tube 18 is placed in communication with the drainage ports 32, as described. Whenever a tube 18 fills to about a three-quarters full condition, another tube 18 is utilized to replace it. Suction to the wound site 104 is continued until drainage ceases. In a large wound, or a wound expected to drain in quantity, two or more wound tubings 10 are emplaced within the wound site 104, to provide for the increased drainage. If desired, other sources of suction within the preferred ranges may be substituted for the tubes 18.

As should now be apparent to a person of ordinary skill in the art, a highly useful and novel drainage system has been disclosed. As should also be apparent, various changes and modifications could be made to the four preferred embodiments of the drainage system. The four preferred embodiments of the drainage system and the method as practiced with the four embodiments of the drainage system are thus illustrative. The scope of the present invention is to be measured by the following claims.

What is claimed is:

1. A drainage system for the removal of a collection of fluids in a region about a wound within the body of a patient, for utilization during healing of the tissue of the wound, comprising:

an elongated tubular member having a distal portion, a proximal portion and an intermediate portion intermediate the distal portion and the proximal portion, the tubular member having a wall with an exterior and defining a centrally located drainage lumen within the wall for the drainage of fluids, an inflation lumen within the wall and separate from the drainage lumen for the passage of inflation fluid, a distal inflation opening through the wall, a plurality of drainage openings through the wall and an inflatable, elastomeric retention balloon on the exterior of the wall, the drainage lumen extending through the proximal portion, the intermediate portion and the distal portion, the inflation lumen being located alongside the drainage lumen and extending through the proximal portion and the intermediate portion, and having a terminus within the intermediate portion, the distal inflation opening being along the intermediate portion between the terminus and the exterior of the intermediate portion for fluid communication of the terminus with the exterior, the drainage openings being along the distal portion between the drainage lumen and the exterior of the distal portion for fluid communication between the exterior and the drainage lumen with potentially obstructing masses being screened from the drainage lumen, and the retention balloon being on the intermediate portion and including an annular sleeve sealed to the exterior of the wall over the distal inflation opening and defining a free space between the sleeve and the wall in fluid communication with the distal inflation opening, the balloon being inflatable upon the introduction of inflation fluid to the free space so as to firmly retain the distal portion of the tubular member in situ adjacent the wound;

a needle adapter member having a distal end sealed to the wall of the proximal portion of the tubular member, the adapter member including a main drainage body extending from the distal end and an inflation arm branching off the main body from adjacent the distal end, the main body having a main body wall defining a drainage passageway and the inflation arm having an inflation arm wall defining an inflation passageway, the drainage passageway being in fluid communication with the drainage lumen through the distal end and the inflation passageway being in fluid communication with the inflation lumen through the distal end, the main body further having an enlarged proximal end defining an enlargement of the drainage passageway and the inflation arm having a free end;

a piercable cap sealed to the enlarged, proximal end of the main body of the adapter member about the exterior thereof;

a disposable, evacuated container having an interior with an open end and a stopper sealed within the open end, the interior being evacuated prior to sealing;

a syringe removably attached to the free end of the inflation arm of the adapter member in fluid communication with the inflation passageway and therethrough with the inflation lumen, the distal inflation opening and the free space of the retention balloon so as to provide and remove pressurized inflation fluid to and from the retention balloon to inflate and deflate the balloon; and a hollow drainage needle having a pointed first end adapted to be pierced through the cap, and a pointed second end adapted to be removably pierced through the stopper, the needle defining a central channel therethrough, the central channel adapted to be in fluid communication with the drainage passageway at the first end and adapted to be in fluid communication with the container interior at the second end, the container interior thereby being in fluid communication with the drainage passageway and therethrough with the drainage lumen, the drainage openings and the collection of fluids in the region of the wound, such that a vacuum may be exerted within the drainage passageway, the drainage lumen and the drainage openings which draws the collection of fluids to the interior of the disposable container, for sanitary disposal upon filling of the disposable container.

2. A drainage system for the removal of a collection of fluids in a region about a wound within the body of a patient, for utilization during healing of the tissue of the wound, as claimed in claim 1, and wherein the main drainage body of the needle adapter member has an integrally formed needle support bridging the drainage passageway from opposite sides of the wall of the proximal end and wherein the needle is permanently inserted through the needle support and the cap, whereby the proximal end of the main drainage body acts as a grip for the needle during insertion of the second end of the needle into the interior of the disposable container.

3. A drainage system for the removal of a collection of fluids in a region about a wound within the body of a patient, for utilization during healing of the tissue of the wound, as claimed in claim 1, and wherein the system further includes a grip and an insertion piece, the grip, insertion piece, cap and needle forming a needle assembly, the grip being pierced by the needle and located between the ends of the needle for manual handling of the needle, the cap being pierced by the needle and located between the ends adjacent the grip and closer the first end than the grip, and the insertion piece being pierced by the needle and located between the ends adjacent the cap and closer the first end than the cap, the insertion piece fitting within the proximal end of the main drainage body and having ridges pressing against and expanding the wall of the proximal end to firmly retain a union of the needle assembly and the needle adapter member.

* * * * *